United States Patent
Tang et al.

(10) Patent No.: US 11,694,773 B2
(45) Date of Patent: Jul. 4, 2023

(54) METHODS TO ESTIMATE EFFECTIVENESS OF A MEDICAL TREATMENT

(71) Applicant: Sanofi, Paris (FR)

(72) Inventors: Qi Tang, Hopewell, NJ (US); Wodan Ling, New York, NY (US); Youran Qi, Madison, WI (US)

(73) Assignee: Sanofi, Paris (FR)

( * ) Notice: Subject to any disclaimer, the term of this patent is extended or adjusted under 35 U.S.C. 154(b) by 717 days.

(21) Appl. No.: 16/790,216

(22) Filed: Feb. 13, 2020

(65) Prior Publication Data
US 2020/0275885 A1    Sep. 3, 2020

Related U.S. Application Data

(60) Provisional application No. 62/812,487, filed on Mar. 1, 2019.

(30) Foreign Application Priority Data

May 21, 2019 (EP) ..................... 19305643

(51) Int. Cl.
| | | |
|---|---|---|
| G06N 5/04 | (2023.01) | |
| G16H 10/20 | (2018.01) | |
| G16H 10/60 | (2018.01) | |
| G06N 20/10 | (2019.01) | |
| A61B 5/00 | (2006.01) | |
| G06N 3/08 | (2023.01) | |
| G06N 5/046 | (2023.01) | |
| G16H 50/70 | (2018.01) | |
| G06F 18/2431 | (2023.01) | |
| G06N 3/048 | (2023.01) | |

(52) U.S. Cl.
CPC .......... *G16H 10/20* (2018.01); *A61B 5/4848* (2013.01); *G06F 18/2431* (2023.01); *G06N 3/048* (2023.01); *G06N 3/08* (2013.01); *G06N 5/046* (2013.01); *G06N 20/10* (2019.01); *G16H 10/60* (2018.01); *G16H 50/70* (2018.01)

(58) Field of Classification Search
None
See application file for complete search history.

(56) References Cited

U.S. PATENT DOCUMENTS

2008/0256006 A1* 10/2008 Buscema ............... G16H 50/50
706/12

OTHER PUBLICATIONS

Lee et al. ("DeepHit: A Deep Learning Approach to Survival Analysis with Competing Risks" 2018) (Year: 2018).*

(Continued)

*Primary Examiner* — Lut Wong
(74) *Attorney, Agent, or Firm* — Fish & Richardson P.C.

(57) ABSTRACT

Implementations of the present disclosure include methods, systems, and computer-readable storage mediums for estimating treatment effect of medical treatments.

20 Claims, 6 Drawing Sheets

(56) References Cited

OTHER PUBLICATIONS

Giannini et al., "Neural networks for beginners. A fast implementation in Matlab, Torch, TensorFlow", Olin Library Cornell University, Mar. 10, 2017, 49 pages.
Mehta et al., "A high-bias, low-variance introduction to machine learning for physicists", Physics Reports 810:1-124, May 2019.
PCT International Search Report and Written Opinion in Application No. PCT/US2020/018051, dated Jun. 5, 2020, 15 pages.
Raposo et al., "Lopinavir resistance classification with imbalanced data using probabilistic neural networks", Journal of Medical Systems, 40(3):69, Mar. 2016.
International Preliminary Report on Patentability in International Application No. PCT/US2020/018051, dated Aug. 25, 2021, 9 pages.

\* cited by examiner

METHODS TO ESTIMATE EFFECTIVENESS OF A MEDICAL TREATMENT

CROSS REFERENCE TO RELATED APPLICATIONS

This application claims priority under 35 U.S.C. § 119(e) to U.S. Application Ser. No. 62/812,487, filed on Mar. 1, 2019, and claims priority to EP Application Serial No. 19305643.9, filed on May 21, 2019, the disclosures of which are incorporated herein by reference.

BACKGROUND

Responder analyses are conducted in clinical data analytics to examine the treatment effect of an investigational product or medical practice to determine how a patient responds to the treatment. A patient is considered as a responder when a response of the patient to a treatment exceeds a threshold.

SUMMARY

Implementations of the present disclosure include computer-implemented methods for estimating treatment effect of a medical treatment. The implementations make such estimation by applying a neural network model on clinical covariates (e.g., blood pressure, heart rate, body temperature, etc.) of patients, and comparing the output for the patients who have used the medical treatment to the output for the patients who have not used the medical treatment. An effectiveness of a medical treatment on a patient can be determined by a response indicator (e.g., a biomarker) that indicates how the patient's body has responded to the medical treatment.

In some implementations, the method includes: receiving, from a database, a dataset comprising: a set of covariate vectors, each covariate vector including clinical covariates of a respective patient, and a set of response indicators, each response indicator being associated with a respective covariate vector, wherein response indicators of the set of response indicators vary over a range; receiving, from the database, multiple partitions on the range of the response indicators to define a plurality of response classes for the response indicator; converting each response indicator to a respective one-hot encoded vector based on response classes indicated by the multiple partitions; training a neural network model based on each covariate vector and a respective one-hot encoded vector associated with the covariate vector, the neural network model utilizing a non-linear activation function and a loss function; and estimating a treatment effect of a medical treatment by: determining a first subset of covariate vectors for patients whom received the medical treatment, and a second subset of covariate vectors for patients whom did not receive the medical treatment, and comparing, for one or more response classes, (i) a first probability to (ii) a second probability, the first probability being a probability that covariate vectors of the first subset of covariate vectors are associated with the one or more response classes, the second probability being a probability that covariate vectors of the second subset of covariate vectors are associated with the one or more response class, wherein the first probability and the second probability are calculated by using the trained neural network model; and providing the estimated treatment effect for displayed on a graphical user interface of a computing device. Other implementations include corresponding systems, apparatus, and computer programs, configured to perform the actions of the methods, encoded on computer storage devices.

In some implementations, the method includes: receiving, from a database, a first dataset comprising: a set of covariate vectors, each covariate vector including clinical covariates of a respective patient, and a set of response indicators, each response indicator being associated with a respective covariate vector, wherein response indicators of the set of response indicators vary over a range; receiving, from the database, multiple partitions on the range of the response indicators to define a plurality of response classes for the response indicator; training a neural network model (NNM) with the first dataset to obtain a first NNM; bootstrapping the first dataset for n times to obtain n second datasets; training the NNM with each second dataset in the n second datasets to obtain n sets of second NNMs; for each covariate vector: obtaining, from the first NNM and the n second NNMs, n+1 predicted responses for the covariate vector, each predicted response being obtained by applying a respective one of the first NNM and the n second NNMs to the covariant vector, and for each response class: estimating an association probability indicating that the covariate vector is associated with the response class by: applying, for the response class, an indicator function to each of the n+1 predicted responses to obtain n+1 outputs for the response class, and calculating the association probability by normalizing an aggregation of the obtained n+1 outputs the response class; estimating a treatment effect of a medical treatment by: determining a first subset of covariate vectors for patients whom received the medical treatment, and a second subset of covariate vectors for patients whom did not receive the medical treatment, and comparing, for one or more response classes, (i) a first normalized aggregation of association probabilities for the first subset, with (ii) a second normalized aggregation of association probabilities of the second subset; and providing the estimated treatment effect for display on a graphical user interface of a computing device.

The present disclosure also provides one or more non-transitory computer-readable storage medium coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

Methods in accordance with the present disclosure may include any combination of the aspects and features described herein. That is, methods in accordance with the present disclosure are not limited to the combinations of aspects and features specifically described herein, but also include any combination of the aspects and features provided.

Among other advantages, the present implementations provide the following benefits. The methods presented herein can be used to predict effectiveness of a medical treatment on a particular patient. An accurate prediction of a treatment effect can provide significant improvement into the medical and health system, including prescribing to a particular patient medical treatments that are predicted as more effective for the particular patient, and eliminating medical treatments that seem less effective from the particular patient's prescriptions, which can result in faster recovery of the patient, fewer side effects that the patient would encounter as a result of taking less effective treatments, and lowering the treatment costs (including monetary, time, use of clinical facilities and healthcare providers).

The present implementations take a non-parametric approach by using a neural network model without making a linearity assumption for the relationship between the model's predictors and the patients' response variables. This approach is advantageous over generalized linear models that model the relationship between predictors and response variables. Such linear models can suffer from loss of power and deviation from linearity assumptions. For example, the response endpoints may not be linearly associated with the covariates of interest, or patient characteristics (e.g., covariates) may not be fully balanced. The present disclosure provides two methods to overcome such limitations. In a first method, the implementations discretize the continuous response variables into categorical variables and apply a neural network model on the categories without making a linearity assumption, and offer an automatic feature representation capability embedded in deep learning methods. A second method builds upon the first method, but does not discretize the continuous response variables. Accordingly, the present implementations improve the estimation accuracy over linear methods by avoiding making a linearity assumptions in the relationship between the predictors and the response variables.

The details of one or more implementations of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Implementations of the present disclosure include computer-implemented methods for estimating treatment effect of medical treatments. The implementations also use deep learning methods to predict the probability of a patient with particular clinical covariates being a responder to a medical treatment.

Figure 1:
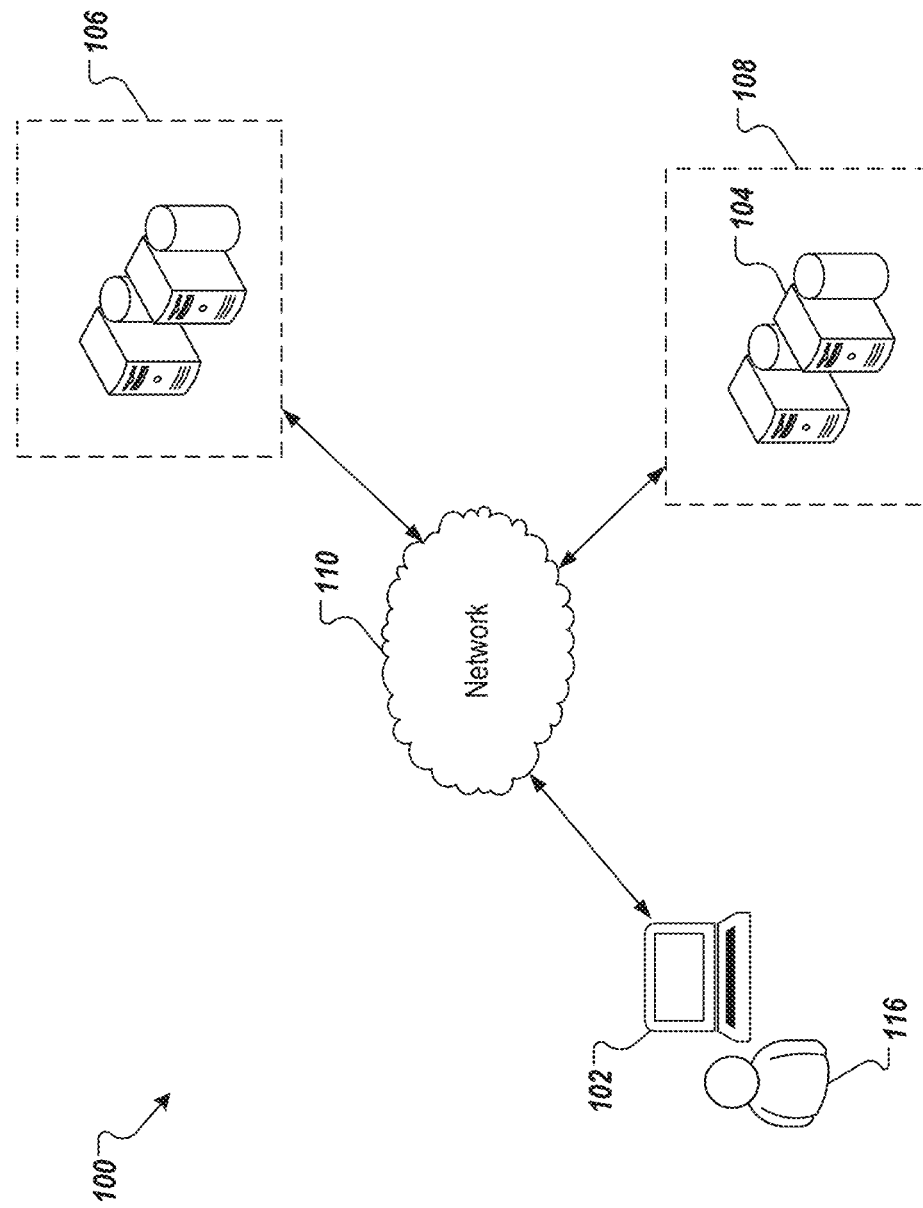
FIG. 1 depicts an example environment that can be used to execute implementations of the present disclosure.

FIG. 1 depicts an example environment 100 that can be used to execute implementations of the present disclosure. The environment 100 illustrates a user 116 that uses a computing device 102 to request an estimate of a treatment effect. The computing device 102 is in communication with a database 106, for example, through a network 110. The database 106 stores clinical covariate data of sample patients. The database 106 provides this data to the computing device 102. The computing device 102 uses this data to train a (deep) neural network model (NNM) and provide an estimate on the probability of effectiveness of the medical treatment (e.g., in general, or for a particular patient). Alternatively, or in addition, the database 106 can provide the data to a computing device 108 that includes one or more processors 104 to perform the estimation procedures.

The NNM can be utilizing a non-linear activation function (e.g., a softmax activation function, a rectified linear unit (ReLu) activation function) and a loss function (e.g., cross-entropy loss, least square error ($L_2$)).

Figure 2:
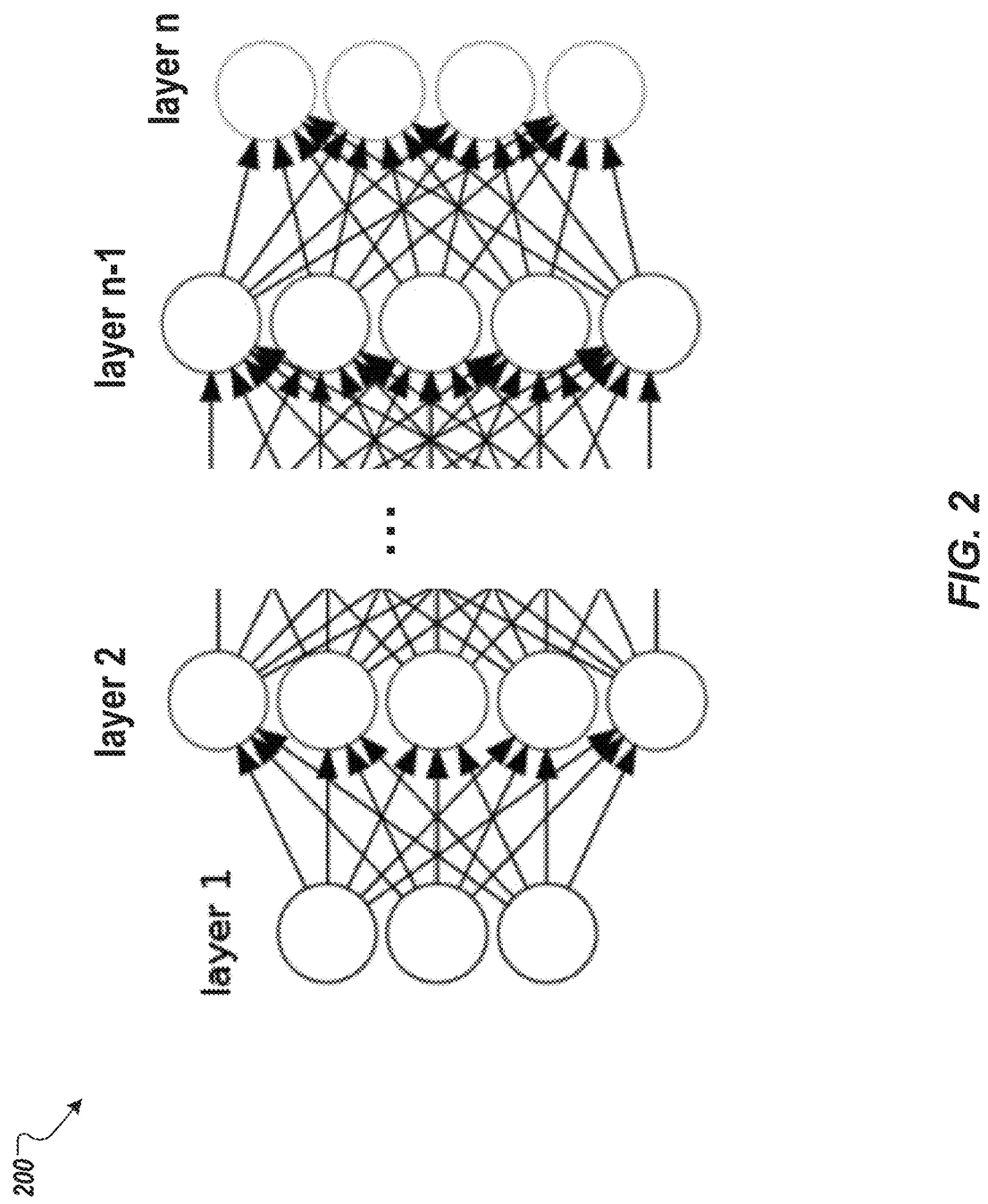
FIG. 2 depicts an example feedforward neural network model that can be used for the implementations of the present disclosure.

The NNM used for calculating the probability can include one or more feedforward NNMs. FIG. 2 illustrates an example feedforward NNM 200 that can be used for the implementations of the present disclosure. The NNM 200 includes multiple layers of computational units interconnected in a feedforward way. Each neuron in one layer has directed connections to the neurons of the subsequent layer. There are numerous choices of the activation function (such as sigmoid, ReLU, etc.) that links neurons in adjacent layers. Parameters of the NNM can be computed by the stochastic gradient descent algorithm. A NNM can be trained by searching for hyperparameters (e.g., number of layers, number of neurons in each layer, etc.) of the NNM based on the NNM's performance on a validation set, for example, to avoid overfitting issues and/or to find the lowest validation error.

In some implementations, only one feedforward neural network is used. Such implementations provide at least two advantages. First, the relationship among multiple outputs can be automatically handled by connections in the lower layers. Second, it is computationally simple and provides the ability to do fast hyperparameter search in a relatively small space. The NNM is denoted by f(X) herein, where X denotes a covariate vector.

Figure 3:
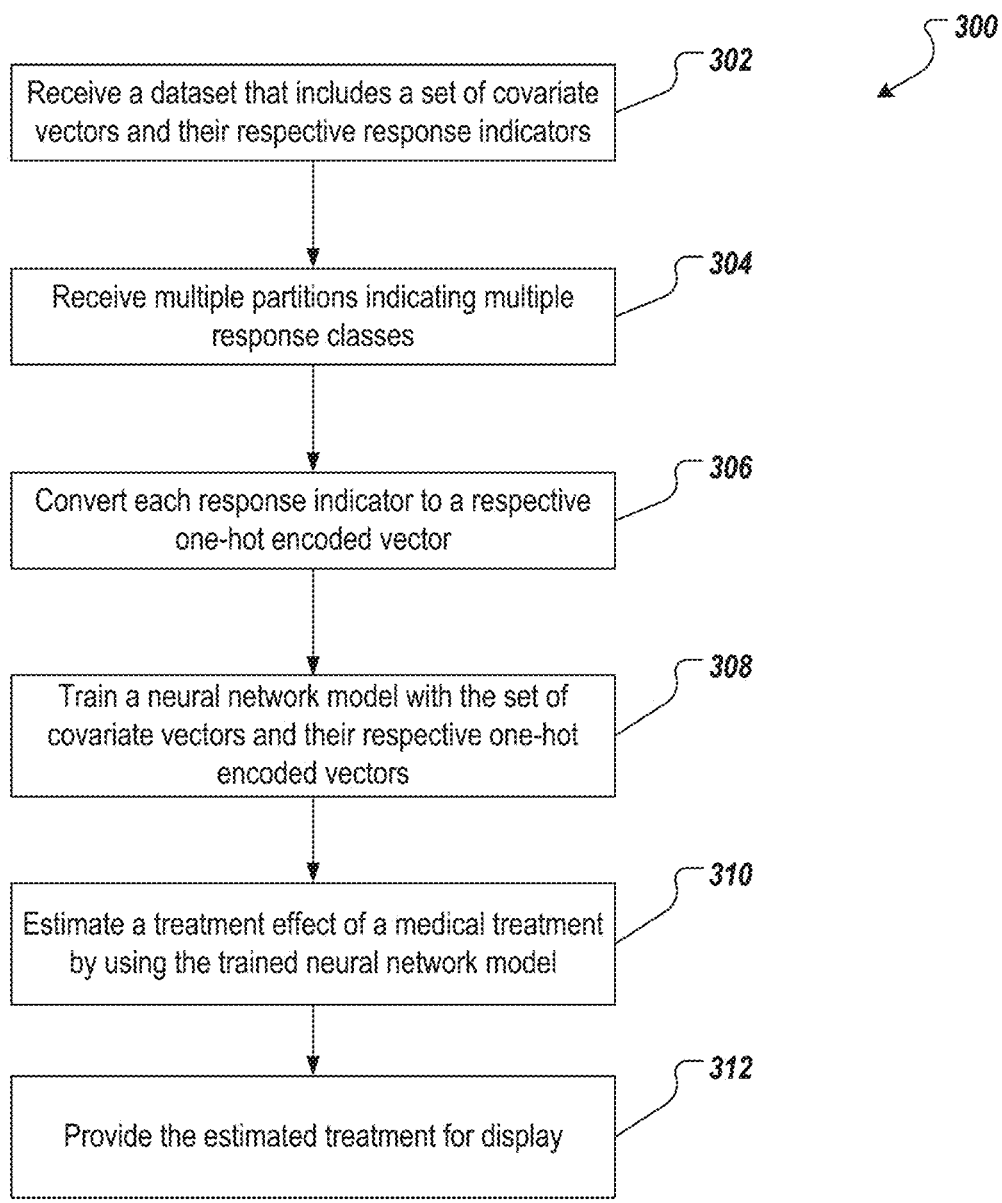
FIG. 3 depicts an example process that can be executed in accordance with implementations of the present disclosure.
Figure 4A:
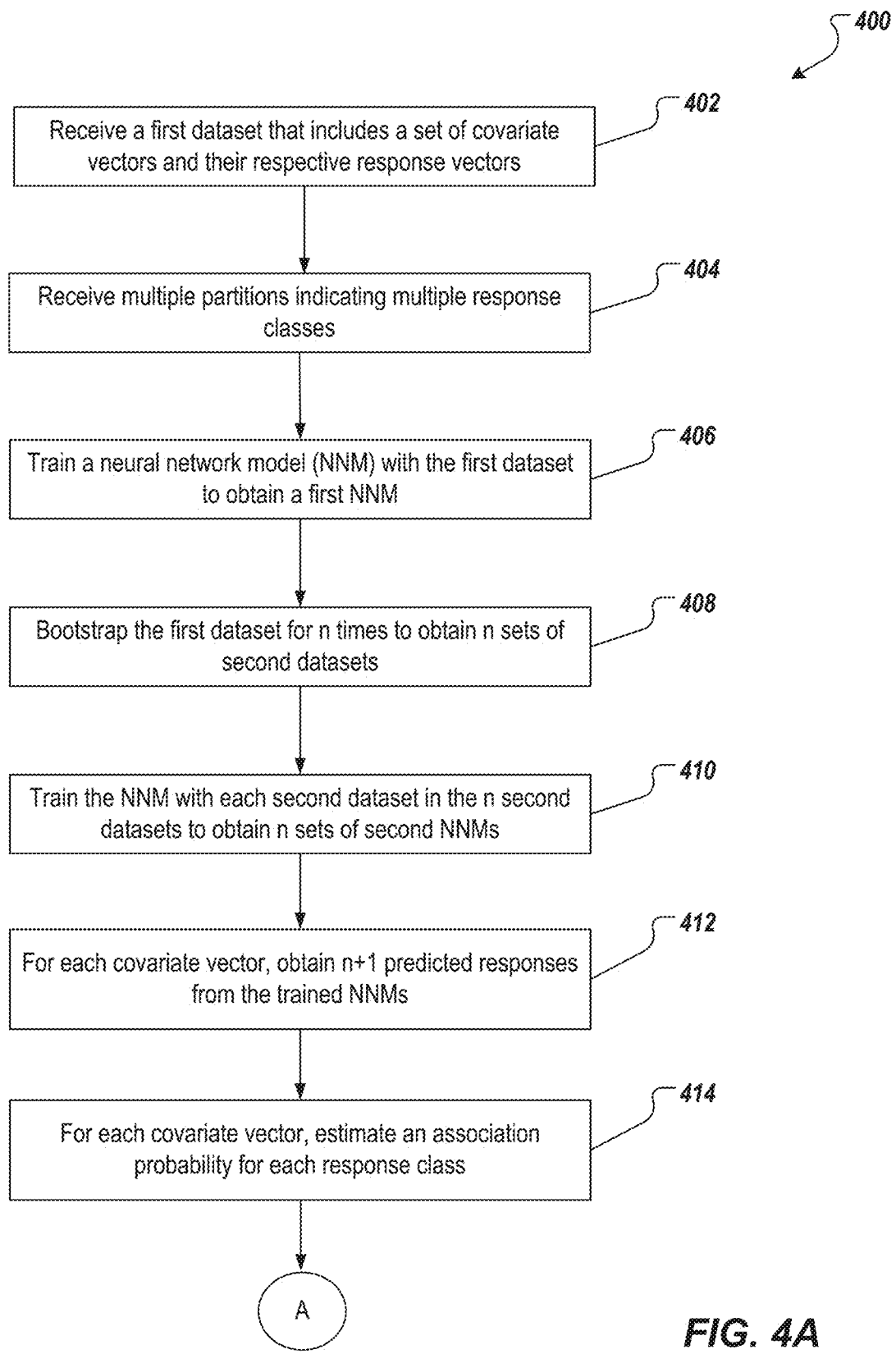
FIGS. 4A-4B depict an example process that can be executed in accordance with implementations of the present disclosure.
Figure 4B:
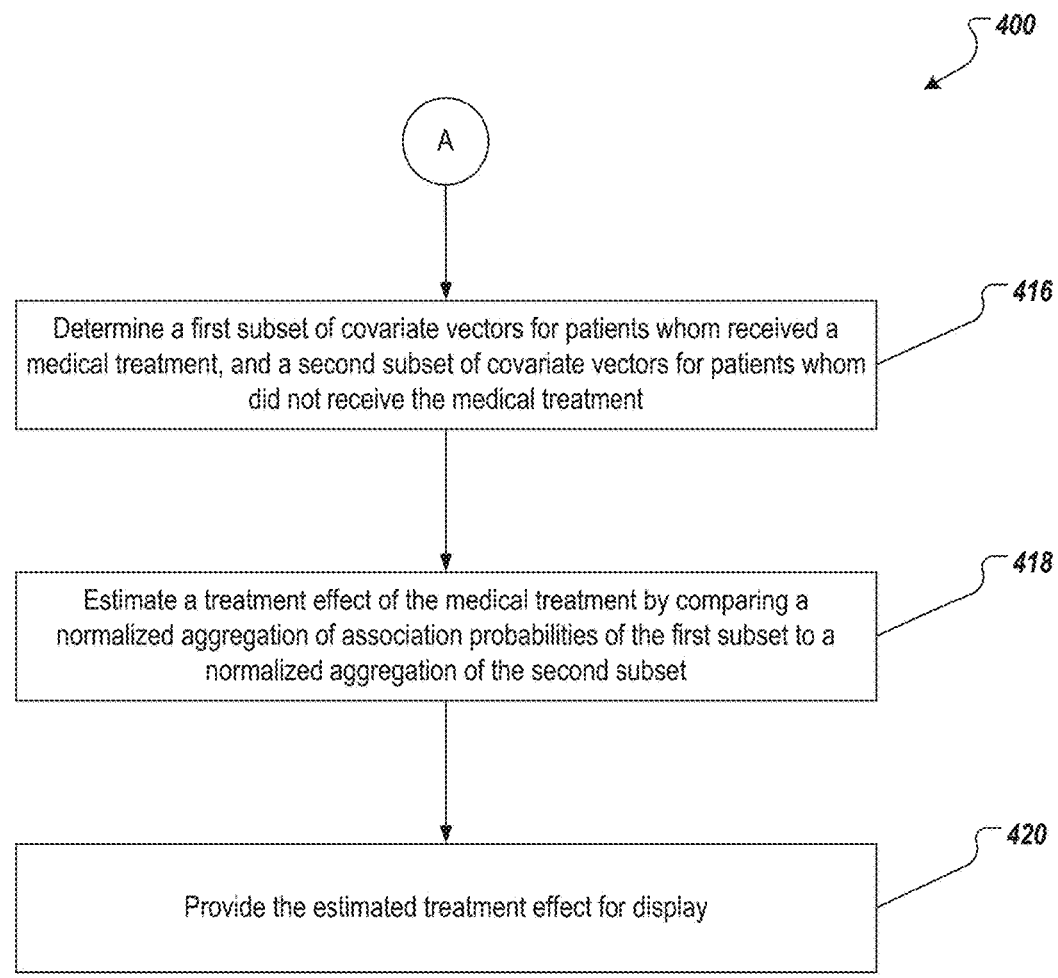

FIGS. 3 and 4A-4B depict two example processes that can be executed in accordance with implementations of the present disclosure to determine an effectiveness of a medical treatment. For ease of description, the processes described herein are categorized into two methods. It would be understood by a skilled artisan that a system may benefit from either or both of these two methods.

First Method:

The first method is depicted in FIG. 3 and can be executed by one or more computing devices (e.g., the computing devices 102 or 108 in FIG. 1). The one or more computing devices receive a dataset $\{(x_i, y_i), i=1, \ldots, q\}$, for example, from a database such as database 106 (302). The dataset includes a set of covariate vectors X and a set of response indicators Y. Each covariate vector $x_i$ includes clinical covariates of a respective patient. Each response indicator (also can be referred to as "endpoint response" or "endpoint responder") $y_i$ is associated with a respective covariate vector $x_i$.

The response indicators vary over a range. The range is partitioned into levels $C_1 < C_2 < \ldots < C_k \in \text{supp}(Y)$. Each $C_j$ represents a response class. In some implementations, the one or more computing devices receives the partitions that indicate the response classes (304), for example, from the database. In some implementations, the computing device receives the partitions from an operator, for example, the user 116.

To determine efficacy of a medical treatment, probabilities of response indicators of the patients is calculated for each response class—i.e., $P(Y<C_1)$, $P(Y<C_2)$, ..., $P(Y<C_k)$. Efficacy of a drug or treatment can be confirmed if the treatment can result in high probabilities for one or more key response classes (for example, two). For example, a percentage change (PCHG) of a key biomarker associated with asthma can be studied to determine the effectiveness of an asthma medicine. The lower the value of the biomarker indicates a healthier condition; thus a lower PCHG indicates a better efficacy of a medical treatment on asthma. In this example, the PCHG is the response indicator. Three partitions of −50%, −25%, and 0 may be used to divide a range of variation of the response indicator into response classes $C_1<-50\%$, $-50\%<C_2<-25\%$, $-25\%<C_3<0$, and $C4>0$. In this example, a higher probability of the PCHG falling in either classes $C_1$ or $C_2$ indicates a more effectiveness of the asthma medicine.

The one or more computing devices convert each of the response indicators received in 302 into a one-hot encoded vector (306) based on the response classes indicated by the partitions. (A one-hot encoded vector is a vector in which only one bit is "on," e.g., having a value of 1 instead of 0.) In other words, the computing devices generate a z, vector for each x, covariate vector (and its respective $y_i$ response indicator) by:

$$z_i=(I(y_i\leq C_1), I(C_1\leq y_i<C_2), \ldots, I(C_{k-1}\leq y_i<C_k), I(y_i\geq C_k)) \quad (1)$$

The one or more computing devices train a NNM (308) with the set of covariate vectors and their respective one-hot encoded vectors—i.e., $\{x_i, z_i\}$ $i=1, 2, \ldots, q$—to obtain a trained NNM model $\hat{f}(x)$.

Applying the trained NNM to each covariate vector $\{x_i\}$ $i=1, \ldots, q$, the trained NNM provides probability of the response class associated with the covariate vector—i.e.:

$$\hat{P}(y_i<C_1), \hat{P}(y_i<C_2), \ldots, \hat{P}(y_i<C_k) \text{ for } i=1,2,\ldots,n.$$

The computing devices estimate (310) the treatment effect of a medical treatment by applying the trained NNM on data $\{x_i, y_i\}$ $i=1, 2, \ldots, q$. To do so, the computing devices determine (or receive from the database) a first subset of covariate vectors for patients who received the medical treatment, and a second subset of covariate vectors for patients who did not receive the medical treatment. The computing devices then compare, for one or more response classes, (i) a first probability to (ii) a second probability. The first probability is a probability that covariate vectors of the first subset covariate vectors are associated with the one or more response classes, and the second probability is a probability that covariate vectors of the second subset of covariate vectors are associated with the one or more response class. The computing device receives the first and the second probabilities from the trained NNM. The one or more response classes (for which the first probability is compared to the second provability,) can be all of the response classes, or particular ones of the response classes (e.g., response classes $C_1<-50\%$ and $-50\%<C_2<-25\%$ in the above example).

More particularly, considering $C_j$ as a key response class and T as a component of X denoting treatment (e.g., T=1 denoting a treatment and T=0 denoting a no-treatment), the treatment effect is calculated by:

$$\hat{\pi}_{C_j}=\hat{P}^{(T=1)}(Y<C_j)-\hat{P}^{(T=0)}(Y<C_j) \quad (2)$$

where $$\hat{P}^{(T=1)}(Y<C_j)=\frac{1}{\Sigma I(t_i=1)}\sum_{t_i=1}\hat{P}(y_i<C_j), \text{ and} \quad (3)$$

$$\hat{P}^{(T=0)}(Y<C_j)=\frac{1}{\Sigma I(t_i=1)}\sum_{t_i=1}\hat{P}(y_i<C_j), \quad (4)$$

Such an aggregated estimator (see equations (3) and (4)) improves accuracy in estimating the treatment effect with reasonably large sample size. Since covariates are correlated and there is no linearity assumption in the (deep) NNM, even with complex relationships among covariates or between covariates and outputs of the NNM, observations (e.g., components of covariate vectors, response indicators) containing real intrinsic associations can be applied to obtain accurate results.

The one or more computing devices provide the estimated treatment effect for presentation. For example, the computing devices can provide the estimated treatment effect for display on a graphical user interface (312), for example, a graphical user interface of the computing device 102 in FIG. 1.

As noted above, probabilities of response indicators of the patients is calculated for each response class—i.e., $P(Y<C_1)$, $P(Y<C_2)$, ..., $P(Y<C_k)$. Using an ordinal classification (or partitioning) on the response indicator range can impose hard constraints on outputs of the NNM. To simplify training of the NNM, the partitioning can be performed as a nominal classification, instead of an ordinal classification. Such nominal classification can provide disjoint response classes, such as $(Y<C_1), (C_1\leq Y<C_2), \ldots, (C_{k-1}\leq Y<C_k), (Y\geq C_k)$. The output of the NNM for these disjoint response classes would be in form of:

$$P(Y<C_1), P(C_1\leq Y<C_2), \ldots, P(C_{k-1}\leq Y<C_k), P(Y\geq C_k),$$

which results in k+1 components in the output. With the trained $\hat{f}(x)$ and a particular set of covariates, the computing devices can obtain the estimated probabilities for response classes of an ordinal classification through accumulating sums:

$$\hat{P}(Y<C_1)=\hat{P}(Y<C_1),$$

$$\hat{P}(Y<C_2)=\hat{P}(Y<C_1)+\hat{P}(C_1\leq Y<C_2),$$

$$\ldots,$$

$$\hat{P}(Y<C_k)=\hat{P}(Y<C_1)+\sum_{j=2}^{k}\hat{P}(C_{j-1}\leq Y<C_j).$$

Such procedure provides the advantages of (i) a one-to-one transformation, with no information loss; and (ii) obtaining a standard classification problem after the transformation, which can be accurately and efficiently addressed by the deep neural network.

The first method described above can include bootstrapping the data received at 302. Bootstrapping can be beneficial when not enough sample is available to train a neural network or when more samples than the available ones are desired for training. Bootstrapping the received data includes bootstrapping (or resampling from) the set of covariate vectors and their respective response indicators. The original data and the bootstrapped data can be used for training and/or validation of the NNM.

Second Method:

The second method is depicted in FIGS. 4A-4B and can be executed by one or more computing devices (e.g., the computing devices 102 or 108 in FIG. 1). The second method eliminates converting (or transforming) the response indicators ($y_i$) to one-hot encoder vectors ($z_i$). Instead, a NNM is used to directly model the relationship between the covariate vectors X and the response indicators Y. As an advantage, eliminating transformation of the response indicators to encoder vectors can reduce power loss.

The second method can include two levels of bootstrapping. The first level is to estimate the probabilities of a patient (or a covariant vector associated with a patient) is a responder to a medical treatment and to calculate effectiveness of a medical treatment based on such probabilities. The second level is to provide uncertainty estimate around the estimated probabilities.

In the first level of bootstrapping, the second method bootstraps the received data for n times to obtain n sets of bootstrapped data. Each set of the bootstrapped data is used to train the NNM and obtain a respective trained NNM, $f^B(X)$. The second method then collects predicted response indicators $\{\hat{y}^{(b_i)}, b_i=1, \ldots, n\}$ that are predicted by the trained NNM $f^{b_i}(X)$ for each of the covariate vectors (Xi). The method estimates an efficacy of a medical treatment based on probabilities of the predicted response indicators (for each covariate vector) being within one or more particular response classes. The following paragraphs provide a detailed description of the second method.

In the second method, the one or more computing devices (noted above,) receive a first dataset $\{(x_i, y_i), i=1, \ldots, q\}$, for example, from a database such as database 106 (402). The first dataset includes a set of covariate vectors X and a set of response indicators Y. Each covariate vector $x_i$ includes clinical covariates of a respective patient. Each response indicator $y_i$ is associated with a respective covariate vector $x_i$.

The response indicators vary over a range. The range is partitioned into levels $C_1 < C_2 < \ldots < C_k \in \text{supp}(Y)$. Each $C_j$ represents a response class. In some implementations, the one or more computing devices receive the partitions that indicate the response classes (404), for example, from the database. In some implementations, the computing device receives the partitions from an operator, for example, the user 116.

The one or more computing devices train a NNM with the first dataset $\{(x_i, y_i), i=1, \ldots, q\}$ to obtain a first NNM (406). The NNM can include a feedforward neural network. The training can include training the NNM using a plurality of hyperparameters, and selecting, for the first NNM, a set of hyperparameters (from the plurality of hyperparameters) that have a lowest validation error.

The computing devices bootstrap the first dataset for n times to obtain n sets of second datasets $\{(x_i, y_i)^{(b_p)}; i=1, \ldots, q; p=1, \ldots, n\}$ (408). The computing devices train the NNM with each of the second datasets to obtain n sets of second NNMs (410). Training one or more of the second NNMs can be done in a process similar to the process of training the first NNM described in the preceding paragraph.

The one or more computing devices obtain n+1 predicted responses for each covariate vector of the first dataset from the trained NNMs (i.e., from the first NNM and the n second NNMs) (412). Each predicted response is obtained by applying a respective one of the first NNM and the n second NNMs to the covariant vector. The obtained predicted responses for a covariate vector $x_i$ can be denoted by $\{\hat{y}_i^{(b_p)}, b_p=1, \ldots, n+1\}$.

A probability of a covariate vector being a responder to a medical treatment can indicate how likely a patient with clinical covariates similar to the covariate vector will respond or have responded to the medical treatment. The computing devices estimate probability of a covariate vector x, being a responder to a medical treatment by estimating an association probability of the covariate vector for one or more key response classes. For example, the computing devices may estimate the association probability for the covariate vector x, for each response class that was identified at 404 (414).

The association probability for a response class for a covariate vector $x_i$ can be calculated by applying an indicator function to each of the n+1 predicted responses to obtain n+1 outputs for the response class, and by normalizing an aggregation of the obtained n+1 outputs. In other words, the association probability for a covariate vector x, in all response classes $C_j$ can be calculated by:

$$\hat{P}(y_i < C_j) = \frac{1}{n} \sum_{b_p=1}^{n} I\left(\hat{y}_i^{(b_p)} < C_j\right) \text{ for } j = 1, \ldots, k. \quad (5)$$

The one or more computing devices estimate a treatment effect of a medical treatment based on association probabilities for the covariate vectors associated with patients who have received the medical treatment, to association probabilities for the covariate vectors of the patients who have not received the medical treatment. More specifically, the computing devices determine (or receive from the database) a first subset of covariate vectors for patients who received the medical treatment, and a second subset of covariate vectors for patients who did not receive the medical treatment (416). The computing devices then compare, for one or more key response classes, (i) a first normalized aggregation of association probabilities for the first subset, with (ii) a second normalized aggregation of association probabilities of the second subset (418). In other words, the computing devices estimate the treatment effect by:

$$\hat{\pi}_{c_j} = \frac{1}{\Sigma I(t_i = 1)} \sum_{t_i=1} \hat{P}(y_i < C_j) - \frac{1}{\Sigma I(t_i = 0)} \sum_{t_i=1} \hat{P}(y_i < C_j), \quad (6)$$

wherein $t_i=1$ denotes treatment cases and $t_i=0$ denotes no-treatment cases. The one or more key response classes can include all of the response classes, or particular ones.

The one or more computing devices provide the estimated treatment effect for presentation. For example, the computing devices can provide the estimated treatment effect for display on a graphical user interface (420), for example, a graphical user interface of the computing device 102 in FIG. 1.

In addition to the above-described procedures, the one or more computing devices can estimate the uncertainty of the estimated treatment effect by using the second level of bootstrapping. In the second level, the uncertainty is estimated by bootstrapping the first dataset for m times to obtain m third datasets, calculating treatment effect for each third dataset in the m third datasets to obtain m treatment effects, and calculating the uncertainty based on a distribution of the m treatment effects. Example uncertainties include, but are not limited to, a confidence interval and a standard deviation of the m treatment effects.

Figure 5:
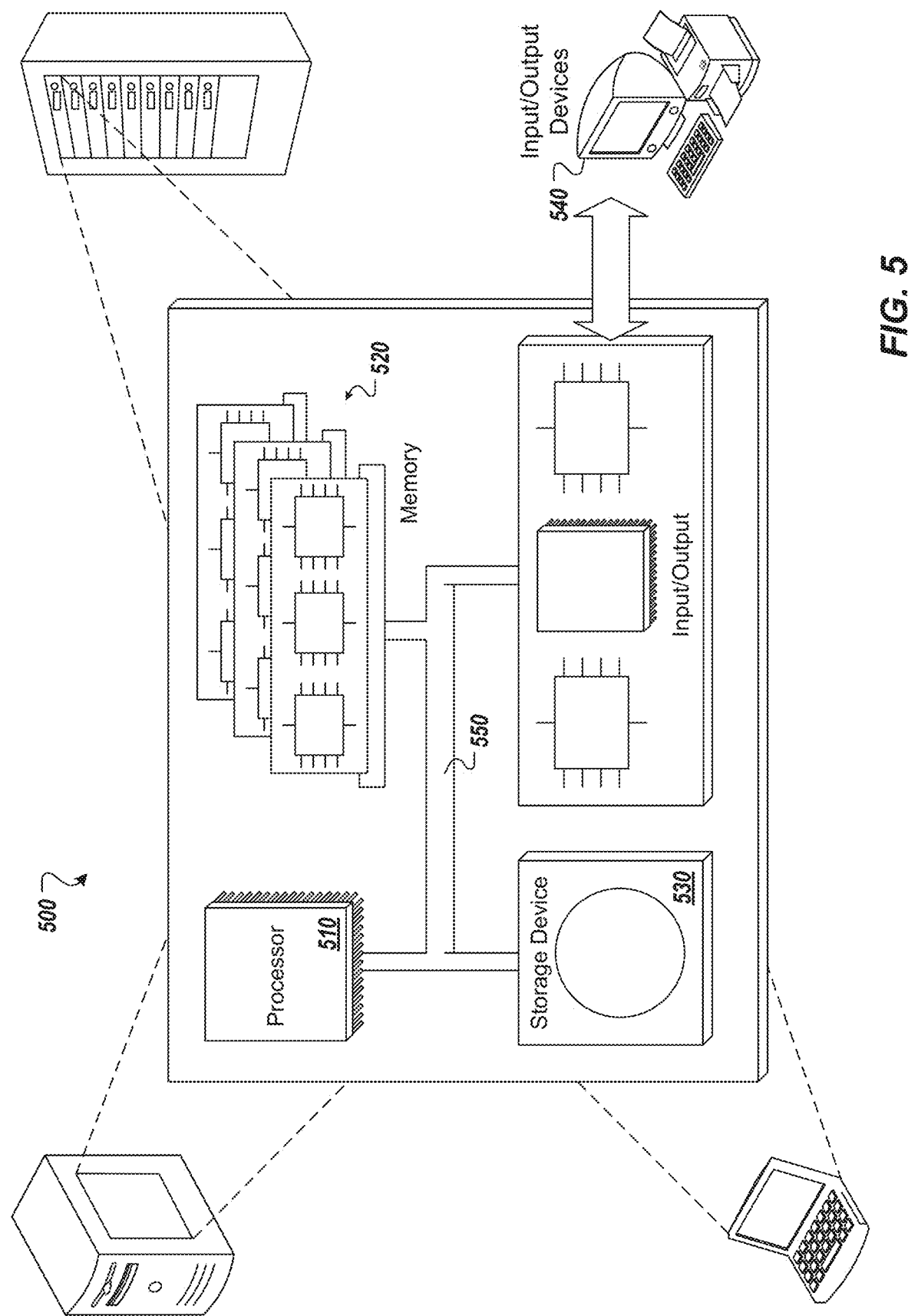
FIG. 5 is a schematic illustration of example computer systems that can be used to execute implementations of the present disclosure.

FIG. 5 depicts a schematic diagram of an example computing system 500. The system 500 may be used to perform the operations described with regard to one or more implementations according to any of the first or the second method of the present disclosure. For example, the system 500 may be included in any or all of the server components, or other computing device(s), discussed herein. The system 500 may include one or more processors 510, one or more memories 520, one or more storage devices 530, and one or more input/output (I/O) devices 540. The components 510, 520, 530, 540 may be interconnected using a system bus 550.

The processor 510 may be configured to execute instructions within the system 500. The processor 510 may include a single-threaded processor or a multi-threaded processor. The processor 510 may be configured to execute or otherwise process instructions stored in one or both of the memory 520 or the storage device 530. Execution of the instruction(s) may cause graphical information to be displayed or otherwise presented via a user interface on the I/O device 540.

The memory 520 may store information within the system 500. In some implementations, the memory 520 is a computer-readable medium. In some implementations, the memory 520 may include one or more volatile memory units. In some implementations, the memory 520 may include one or more non-volatile memory units.

The storage device 530 may be configured to provide mass storage for the system 500. In some implementations, the storage device 530 is a computer-readable medium. The storage device 530 may include a floppy disk device, a hard disk device, an optical disk device, a tape device, or other type of storage device. The I/O device 540 may provide I/O operations for the system 500. In some implementations, the I/O device 540 may include a keyboard, a pointing device, or other devices for data input. In some implementations, the I/O device 540 may include output devices such as a display unit for displaying graphical user interfaces or other types of user interfaces.

The features described may be implemented in digital electronic circuitry, or in computer hardware, firmware, software, or in combinations of them. The apparatus may be implemented in a computer program product tangibly embodied in an information carrier (e.g., in a machine-readable storage device) for execution by a programmable processor; and method steps may be performed by a programmable processor executing a program of instructions to perform functions of the described implementations by operating on input data and generating output. The described features may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language, including compiled or interpreted languages, and it may be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Elements of a computer may include a processor for executing instructions and one or more memories for storing instructions and data. Generally, a computer may also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, application-specific integrated circuits (ASICs).

To provide for interaction with a user, the features may be implemented on a computer having a display device such as a cathode ray tube (CRT) or liquid crystal display (LCD) monitor for displaying information to the user and a keyboard and a pointing device such as a mouse or a trackball by which the user may provide input to the computer.

The features may be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system may be connected by any form or medium of digital data communication such as a communication network. Examples of communication networks include, e.g., a local area network (LAN), a wide area network (WAN), and the computers and networks forming the Internet.

The computer system may include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A computer-implemented method executed by one or more processors, the method comprising:
  receiving, from a database, a dataset comprising:
    a set of covariate vectors, each covariate vector including clinical covariates of a respective patient, and
    a set of response indicators, each response indicator being associated with a respective covariate vector, wherein response indicators of the set of response indicators vary over a range;
  receiving, from the database, multiple partitions on the range of the response indicators to define a plurality of response classes for the response indicator;

converting each response indicator to a respective one-hot encoded vector based on response classes indicated by the multiple partitions;
training a neural network model based on each covariate vector and a respective one-hot encoded vector associated with the covariate vector; and
estimating a treatment effect of a medical treatment by:
determining a first subset of covariate vectors for patients who received the medical treatment, and a second subset of covariate vectors for patients who did not receive the medical treatment, and
comparing, for one or more response classes, (i) a first probability to (ii) a second probability, the first probability being a normalized aggregation of respective probabilities that covariate vectors of the first subset of covariate vectors are associated with the one or more response classes, the second probability being a normalized aggregation of respective probabilities that covariate vectors of the second subset of covariate vectors are associated with the one or more response class,
wherein the respective probabilities are calculated by using the trained neural network model; and
providing the estimated treatment effect for display on a graphical user interface of a computing device.

2. The method of claim 1, wherein the neural network model utilizes a non-linear activation function and a loss function.

3. The method of claim 1, wherein in estimating the treatment effect, the one or more response classes comprises all of the plurality of response classes.

4. The method of claim 1, wherein training the neural network model further comprises bootstrapping the set of covariate vectors and the set of response indicators.

5. The method of claim 1, wherein at least two response classes in the plurality of response classes are disjoint.

6. The method of claim 1, wherein the neural network model utilizes a softmax activation function and a cross-entropy loss function.

7. The method of claim 1, wherein the neural network is a feedforward neural network.

8. A computer-implemented method executed by one or more processors, the method comprising:
receiving, from a database, a first dataset comprising:
a set of covariate vectors, each covariate vector including clinical covariates of a respective patient, and
a set of response indicators, each response indicator being associated with a respective covariate vector, wherein response indicators of the set of response indicators vary over a range;
receiving, from the database, multiple partitions on the range of the response indicators to define a plurality of response classes for the response indicator;
training a neural network model (NNM) with the first dataset to obtain a first NNM;
bootstrapping the first dataset for n times to obtain n second datasets;
training the NNM with each second dataset in the n second datasets to obtain n sets of second NNMs;
for each covariate vector:
obtaining, from the first NNM and the n second NNMs, n+1 predicted responses for the covariate vector, each predicted response being obtained by applying a respective one of the first NNM and the n second NNMs to the covariant vector, and
for each response class:
estimating an association probability indicating that the covariate vector is associated with the response class by:
applying, for the response class, an indicator function to each of the n+1 predicted responses to obtain n+1 outputs for the response class, and
calculating the association probability by normalizing an aggregation of the obtained n+1 outputs for the response class;
estimating a treatment effect of a medical treatment by:
determining a first subset of covariate vectors for patients who received the medical treatment, and a second subset of covariate vectors for patients who did not receive the medical treatment, and
comparing, for one or more response classes, (i) a first normalized aggregation of association probabilities for the first subset, with (ii) a second normalized aggregation of association probabilities of the second subset; and
providing the estimated treatment effect for display on a graphical user interface of a computing device.

9. The method of claim 8, wherein the one or more response classes comprises all of the plurality of response classes.

10. The method of claim 8, further comprising estimating an uncertainty on the treatment effect by:
bootstrapping the first dataset for m times to obtain m third datasets;
calculating treatment effect for each third dataset in the m third datasets to obtain m treatment effects; and
calculating the uncertainty based on a distribution of the m treatment effects.

11. The method of claim 10, wherein the uncertainty on the treatment effect includes at least one of a confidence interval and a standard deviation of the m treatment effects.

12. The method of claim 8, wherein the NNM utilizes a non-linear activation function and a least square error loss function.

13. The method of claim 12, wherein the non-linear activation function is a rectified linear unit (ReLU) function.

14. The method of claim 8, wherein the training the NNM with the first dataset to obtain the first NNM comprises:
training the NNM using a plurality of hyperparameters; and
selecting, for the first NNM, a set of hyperparameters that have a lowest validation error, the set of hyperparameters being selected from the plurality of hyperparameters.

15. A non-transitory, computer-readable medium storing one or more instructions executable by a computer system to perform operations comprising:
receiving a dataset comprising:
a set of covariate vectors, each covariate vector including clinical covariates of a respective patient, and
a set of response indicators, each response indicator being associated with a respective covariate vector, wherein response indicators of the set of response indicators vary over a range;
receiving multiple partitions on the range of the response indicators to define a plurality of response classes for the response indicator;
converting each response indicator to a respective one-hot encoded vector based on response classes indicated by the multiple partitions;
training a neural network model based on each covariate vector and a respective one-hot encoded vector associated with the covariate vector, the neural network model utilizing a non-linear activation function and a loss function; and estimating a treatment effect of a medical treatment by:
determining a first subset of covariate vectors for patients who received the medical treatment, and a second subset of covariate vectors for patients who did not receive the medical treatment, and comparing, for one or more response classes, (i) a first probability to (ii) a second probability, the first probability being a normalized aggregation of respective probabilities that covariate vectors of the first subset of covariate vectors are associated with the one or more response classes, the second probability being a normalized aggregation of respective probabilities that covariate vectors of the second subset of covariate vectors are associated with the one or more response class, wherein the respective probabilities are calculated by using the trained neural network model; and providing the estimated treatment effect for display on a graphical user interface of a computing device.

16. The non-transitory, computer-readable medium of claim 15, wherein in estimating the treatment effect, the one or more response classes comprises all of the plurality of response classes.

17. The non-transitory, computer-readable medium of claim 15, wherein training the neural network model further comprises bootstrapping the set of covariate vectors and the set of response indicators.

18. The non-transitory, computer-readable medium of claim 15, wherein at least two response classes in the plurality of response classes are disjoint.

19. The non-transitory, computer-readable medium of claim 15, wherein the neural network model utilizes a softmax activation function and a cross-entropy loss function.

20. The non-transitory, computer-readable medium of claim 15, wherein the neural network is a feedforward neural network.

* * * * *